(12) United States Patent
Ogata et al.

(10) Patent No.: US 11,969,276 B1
(45) Date of Patent: Apr. 30, 2024

(54) DUAL HEAD X-RAY INSPECTION SYSTEM

(71) Applicant: Xwinsys Technology Development Ltd., Migdal HaEmek (IL)

(72) Inventors: Kiyoshi Ogata, Tokyo (JP); Avishai Shklar, Kfar Vitkin (IL); Doron Reinis, Gival Ela (IL); Ofek Oiknine, Ramat Yishai (IL)

(73) Assignee: Xwinsys Technology Development Ltd., Migdal HaEmek (IL)

( * ) Notice: Subject to any disclaimer, the term of this patent is extended or adjusted under 35 U.S.C. 154(b) by 0 days.

(21) Appl. No.: 18/142,161

(22) Filed: May 2, 2023

(30) Foreign Application Priority Data

Mar. 9, 2023 (IL) .......................................... 301287

(51) Int. Cl.
*A61B 6/00* (2006.01)
*A61B 6/40* (2024.01)
*A61B 6/42* (2024.01)
*G01N 23/00* (2006.01)

(52) U.S. Cl.
CPC .......... *A61B 6/4035* (2013.01); *A61B 6/4241* (2013.01); *A61B 6/485* (2013.01)

(58) Field of Classification Search
CPC .......................... G01N 2223/06; G01N 23/223
See application file for complete search history.

(56) References Cited

U.S. PATENT DOCUMENTS

| | | | |
|---|---|---|---|
| 8,249,220 B2 | 8/2012 | Verman et al. | |
| 10,697,908 B2 | 6/2020 | Reinis et al. | |
| 2004/0213373 A1 | 10/2004 | Wilson et al. | |
| 2008/0159474 A1 | 7/2008 | Hubbard-Nelson et al. | |
| 2013/0034204 A1* | 2/2013 | Matoba | G01N 23/223 378/44 |
| 2021/0116399 A1 | 4/2021 | Ogata et al. | |

* cited by examiner

*Primary Examiner* — Dani Fox
(74) *Attorney, Agent, or Firm* — Dorsey & Whitney LLP

(57) ABSTRACT

A sample inspection system is described. The system comprises at least first and second inspection units positioned above a sample region. Each of said at least first and second inspection unit comprises at least one X-ray radiation source and respective detector arrangement and configured for X-ray fluorescent inspection of a sample. Wherein the first and second x-ray inspection units provide first and second inspection properties different in at least one of: bandwidth of emitted X-ray energies, energy of emitted X-rays, spot size of X-ray beam generated on a sample.

20 Claims, 13 Drawing Sheets

DUAL HEAD X-RAY INSPECTION SYSTEM

TECHNOLOGICAL FIELD

The present disclosure is in the field of sample inspection system, and specifically relates to inspection using X-Ray fluorescence of samples.

BACKGROUND

Inspection of fabricated samples is an important part of manufacturing processes. Various manufactured articles may be inspected for structural parameters, selected patterns, and material composition. With technological advances, the manufactured articles become smaller and required inspection accuracy is increased.

X-ray fluorescence (XRF) inspection provides is a non-destructive technique enabling detection of elemental composition of materials. XRF inspection utilizes fluorescence caused by excitation of sample material by X-ray radiation provided by an x-ray source. Atoms of different elements produce characteristic fluorescence emission unique to each element, allowing detection of material composition of a sample. Energy dispersive X-ray Fluorescence (EDXRF) is one of several XRF techniques commonly used in elemental analysis applications, enabling detection of various elements existing in a sample material.

U.S. Pat. No. 10,697,908 provides a method and an apparatus for apparatus for inspecting a semiconductor wafer for abnormalities by accurately measuring elemental concentration at a target area. The apparatus includes an x-ray imaging subsystem for measuring an elemental composition at the target area of the semiconductor wafer. The apparatus further includes an EDXRF subsystem for measuring an elemental concentration at the target area of the semiconductor wafer. The elemental concentration may be calibrated by first correlating the elemental concentration measurements obtained using x-ray imaging system for the target area with the elemental concentration measurements obtained using the EDXRF subsystem for the target area to receive an augmented and accurate elemental concentration measurement for the target area of the semiconductor wafer.

U.S. Pat. No. 8,249,220 provides an x-ray optical system includes an x-ray source which emits x-rays, a first optical element which conditions the x-rays to form two beams and at least a second optical element which further conditions at least one of the two beams from the first optical element.

GENERAL DESCRIPTION

A complete inspection of a manufactured sample may often require inspection using two or more different inspection conditions. This may require inspection of a sample using two or more different inspection systems, or replacement of an inspection unit within an existing inspection system. The present disclosure provides an inspection system configuration utilizes two or more inspection units, simultaneously positioned over a sample region of an inspection system. The two or more inspection units are configured for sample inspection using two or more respective and different inspection conditions, enabling detection of various parameters of the sample.

Generally, according to some aspects, the present disclosure provides an inspection system comprising at least first and second inspection units positioned above a sample inspection region. Each of said at least first and second inspection unit comprises at least one X-ray radiation source and respective detector arrangement and configured for X-ray fluorescent inspection of a sample. According to the present disclosure X-ray radiation source of said first inspection unit is configured to emit monochromatic X-ray radiation, and X-ray radiation source of said second inspection unit is configured to emit polychromatic X-ray radiation.

This arrangement enables complete inspection of material composition of a sample by identifying and quantifying elements of the periodic table within the sample. More specifically, the use of polychromatic X-ray radiation for inspection of sample, e.g., for elemental inspection, enables detection of a broad range of elements. However, the use of polychromatic radiation, covering wide band of X-ray energies generates relatively high background radiation acting as noise. This may limit detection sensitivity to elements existing in low concentration (amount) in the sample. Alternatively, inspection using monochromatic X-ray radiation enables reducing the background noise and thus provides for sensitive detection of elements having fluorescent response to radiation within illumination energy band even for low concentrations. In this connection, inspection using monochromatic X-ray radiation as described in the present disclosure relates to the use of X-ray radiation within one or more discrete energy bands. The generally-discrete radiation pattern is typically provided using one or more multilayer optical elements filtering X-ray radiation provided by an X-ray source. Following filtering by the multilayer optical elements, the X-ray radiation is filtered by one or more band-pass filters providing one or more discrete energy bands of X-ray radiation directed at the sample.

The use of monochromatic X-ray radiation for inspection thus enables high sensitivity for detection properties of selected elements that may exist in the sample in low amounts or concentrations. This is while the use of polychromatic X-ray radiation is known to provide efficient and robust detection of a wide range of elements and respective detection energies.

In this connection, typical polychromatic X-ray radiation suitable of EDXRF inspection relates to emission energies in a range between 2.5 KeV and 30 KeV. Typical polychromatic inspection unit may generally emit radiation within certain predetermined profile within such range. Differently, as described herein, the term monochromatic inspection, is used herein as relative to inspection using one or more discrete bands of relatively narrow energy bandwidth. For example, monochromatic inspection unit may utilize inspection using one, two, three or four energetically separated bands having typical bandwidth of 2 KeV, or preferably of 1 KeV, or more preferably having bandwidth of 500 eV. As a result, the emission spectrum of monochromatic inspection unit may include a selected number of separated emission lines within the broad X-ray spectrum.

The inspection system of the present disclosure thus enables complete inspection of samples for material composition at high spatial resolution along the sample, utilizing inspection system having generally conventional form-factor and eliminating the need for additional inspection systems and transferring the sample between them. This effectively provides several advantages including, but not limited to, the following:
  a complete elemental inspection of a sample within form factor of a single inspection system;
  eliminating, or at least significantly reducing moving parts above a sample region during inspection, this greatly reduces sample contamination;

common spatial registration of sample inspection that is not associated with variation of possible manufacturing errors in stage translation;

enabling parallel inspection, suitable of relatively large and uniform samples.

To enable common mounting of at least first and second inspection unit over a sample region, the present disclosure further provides a system comprising: a chassis structure; a sample mount configured for holding one or more samples and enabling translation of said one or more samples within a sample region; an inspection system mounting arrangement comprising at least first and second support beams attached to said chassis, said at least first and second support beams comprise at least horizontal portion stretching above said sample region; and a horizontal beam mounted on said at least first and second support beams and positioned above said sample region, said horizontal beam comprises mounting arrangement for mounting at least first and second X-ray fluorescence inspection units simultaneously to enable operation of said at least first and second X-ray fluorescence inspection units by translation shifts of a sample within said sample region.

Arrangement of the horizontal beam mounted on at least first and second support beams provides structural stability of the system holding weight of said at least first and second X-ray fluorescence inspection units. Additionally, configuration of the horizontal beam and its support beams provides unobstructed access to the sample region for inserting, extracting and otherwise performing various operations on a sample within the system.

Thus, according to a broad aspect, the present disclosure provides a sample inspection system comprising:

at least first and second inspection units positioned above a sample inspection region, each of said at least first and second inspection unit comprises at least one X-ray radiation source and respective detector arrangement and configured for X-ray fluorescent inspection of a sample; wherein said at least first and second x-ray inspection units provide first and second inspection properties different in at least one of: bandwidth of emitted X-ray energies, energy of emitted X-rays, spot size of X-ray beam generated on a sample.

According to some embodiments, at least one of said first and second X-ray inspection unit may comprise a monochromatic X-ray radiation source.

According to some embodiments, the first and second X-ray inspection units may be configured to provide monochromatic X-ray illumination having one or more central illumination energies with bandwidth of up to 2 KeV around said one or more central illumination energies, and wherein said first and second inspection units provide first and second inspection properties different in at least one of: said one or more central illumination energies of emitted X-rays and spot size of X-ray beam generated on a sample.

According to some other embodiments, the first inspection unit may be configured to emit X-ray radiation formed of one or more discrete energy bands, and said second inspection unit is configured to emit continuous spectrum of polychromatic X-ray radiation.

The first inspection unit may comprise an optical arrangement comprising one or more multilayer optical elements configured to provide band-pass filtering to X-ray radiation directed thereon, thereby providing illumination pattern having one or more discrete energy bands.

According to some embodiments, the at least first and second inspection units may be mounted on a common mounting arrangement, said common mounting arrangement comprises a horizontal beam positioned above a dedicated sample region, said horizontal beam is supported by at least two support beams located at different sides of said dedicated sample region.

The horizontal beam may be supported by two support beams, each of said support beams are formed having a first, generally vertical, portion extending upward from a bottom frame of said system and a second, generally horizontal, portion extending horizontally from said first portion and connected to said horizontal beam.

The support beams may be formed with an inverted "L" shape, having generally horizontal portion extending above said dedicated sample region and placing said horizontal beam above said dedicated sample region.

According to some embodiments, the sample inspection system may further comprise at least one optical microscope unit mounted on said horizontal beam.

According to some embodiments, the sample inspection system may comprise at least first and second optical microscope units having respectively first and second different focal lengths, thereby enabling adjustment of field of view for optical microscopy while obviating the need for moving optical elements during sample inspection.

According to some embodiments, the at least first and second inspection units may be mounted on said horizontal beam via respective first and second dedicated connectors, said first and second dedicated connectors comprise a horizontal portion configured to mount said connector on a top surface of said horizontal beam and a vertical portion extending along a vertical wall of said horizontal beam, and wherein said vertical portion is connectable to the respective one of said at least first and second inspection units.

According to some embodiments, at least one of said first and second connectors may further comprise a lower edge (ridge) positioned to lock onto a bottom part of said horizontal beam.

According to some embodiments, the sample inspection system may further comprise a moveable sample platform positioned in said sample inspection region and adapted for placing a sample for inspection, said moveable sample mount has planar moving range enabling inspection by each one of said at least first and second inspection units.

According to some embodiments, elements of said at least first and second inspection units are stationary during sample inspection, thereby eliminating sample contamination associated with moving elements above the sample.

According to another broad aspect, the present disclosure provides a system comprising:

a chassis structure;

a sample mount configured for holding one or more samples and enabling translation of said one or more samples within a sample region;

an inspection system mounting arrangement comprising at least first and second support beams attached to said chassis, said at least first and second support beams comprise at least horizontal portion stretching above said sample region; and a horizontal beam mounted on said at least first and second support beams and positioned above said sample region, said horizontal beam comprises mounting arrangement for mounting at least first and second X-ray fluorescence inspection units simultaneously, to enable operation of said at least first and second X-ray fluorescence inspection units by translation shifts of a sample within said sample region.

According to some embodiments, the horizontal beam may further comprise mounting arrangement for mounting of at least first and second optical microscopes in addition to said at least first and second X-ray fluorescence inspection units.

According to some embodiments, the at least first and second support beams may comprise a vertical portion attached to said chassis laterally to said sample region, and wherein said at least horizontal portion extends from a top part of said vertical portion above said sample region, and wherein mounting arrangement of said horizontal beam are placed above said sample region.

According to some embodiments, the mounting arrangement for mounting at least first and second X-ray fluorescence inspection units may comprise attachment points on at least two of top, side, and bottom surfaces of said horizontal beam.

According to some embodiments, the system may further comprise at least first and second X-ray fluorescence inspection units mounted on the respective mounting arrangement, each of said at least first and second X-ray fluorescence inspection unit comprises at least one X-ray radiation source and respective detector arrangement; wherein said first inspection unit comprises one or more multilayer radiation filters configured to filter X-ray radiation to provide inspection using one or more discrete energy bands, and said second inspection unit is configured to emit continuous polychromatic X-ray radiation.

According to some embodiments, the sample mount may comprise translation arrangement enabling selective translation of a sample within said sample region allowing selective positioning of said sample below each one of mounting arrangement positions.

According to yet a further broad aspect, the present disclosure provides a method for XRF inspection of a sample, the method comprising: providing said sample to an inspection system; inspecting said sample using a first x-ray inspection unit having first set of inspection properties and generating first output inspection data; processing said first output inspection data and determining one or more regions of said sample to be inspected by a second x-ray inspection unit; translating said sample within said inspection system to location of a second x-ray inspection unit; inspecting said sample using a second x-ray inspection unit having second set of inspection properties and generating second output inspection data; aligning said first and second output inspection data and processing said first and second output inspection to determine sample properties.

According to some embodiments, the method may further comprise: determining a first registration position associated with inspection using said first x-ray inspection unit; determining a second registration position associated with inspection using said second x-ray inspection unit; and using said first and second registration positions for aligning said first and second output inspection data.

According to some embodiments, at least one of the first and second x-ray inspection units is a monochromatic x-ray inspection unit utilizing monochromatic x-ray radiation source.

According to some embodiments, the method may further comprise operating at least one optical microscope for optical inspection of the sample, and processing output data of said optical inspection to determine one or more selected locations of the sample for inspection using at least one of first and second x-ray inspection units.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
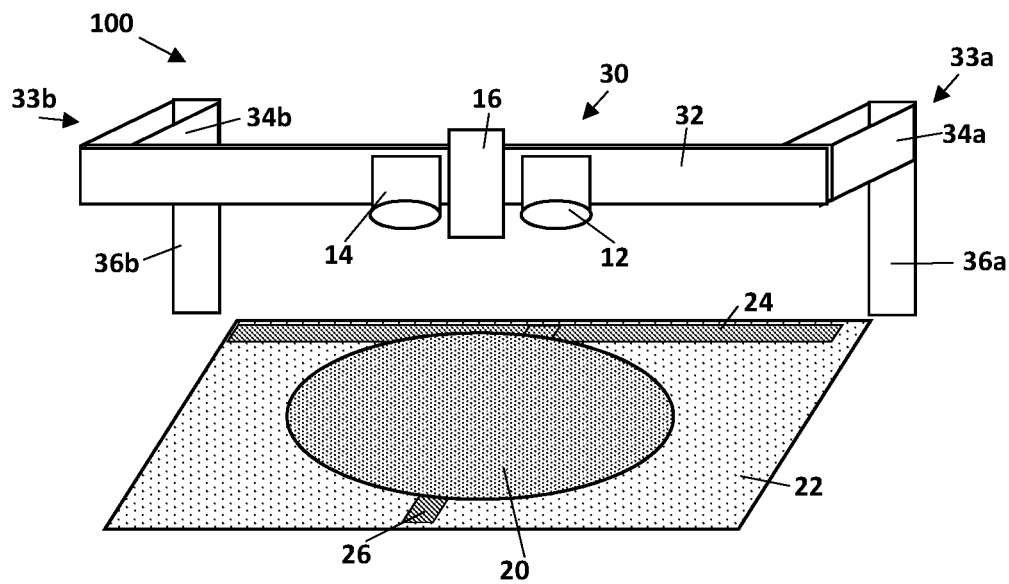
FIG. 1 schematically illustrates an inspection system according to some embodiments of the present disclosure.

As indicated above, the present disclosure provides a novel inspection system configuration enabling efficient inspection of various samples utilizing two or more inspection heads within a common system. In this connection, reference is made to FIG. 1 exemplifying a sample inspection system 100 according to some embodiments. The system 100 includes at least first 12 and second 14 inspection units mounted on a common beam 30 and positioned to enable inspection of a sample located on sample mount 20.

The sample mount 20 is moveable within a sample region 22 (or sample inspection region) using translation system exemplified herein by first and second linear translation elements 24 and 26.

The inspection units 12 and 14 are positioned on an inspection system mounting including at least a horizontal beam 30 positioned above a sample region 22. In this exemplary configuration, the horizontal beam 30 is held in place over the sample region 22 by first and second support beams 33a and 33b, each including a first horizontal portion 34a and 34b. The horizontal portions 34a and 34b of the support beams 33a and 33b stretch above the sample region 22 providing a generally free access to the sample region 22 for placing, removing, and otherwise manipulating a sample thereon.

As further exemplified in FIG. 1, the support beams may be formed in an inverted "L" shape including a first horizontal portion 34a and 34b, and a second vertical portion 36a and 36b. The vertical portions 36a and 36b are mounted on chassis of the system 100 extending vertically to a selected height above the sample region 22. At a selected height, horizontal portions 34a and 34b extend from the vertical portions 36a and 36b toward center of the sample region 22.

Generally, the first 12 and second 14 inspection units are X-Ray inspection units configured to provide X-ray illumination onto an illumination spot located under the inspection unit, and to collect response radiation from a sample that may be placed on the sample mount 20. In addition to the first 12 and second 14 X-ray inspection units, the system 100 may also include one or more optical microscopes 16. The one or more optical microscopes may be used to collect optical image data of a sample located within the system 100, to enable proper alignment of the sample to the X-ray inspection units. In some preferred embodiments of the present disclosure the system may include two or more optical microscopes configured with selected two or more different magnification levels.

As indicated above, the at least first 12 and second 14 inspection units may be X-ray inspection units. In some embodiments of the present disclosure, the x-ray inspection unit may be configured to provide Energy Dispersive X-ray Fluorescence (EDXRF) inspection of a sample. Generally, EDXRF is a nondestructive technique for elemental analysis of a sample. The technique is based on analysis of X-ray fluorescent response of a sample in response to X-ray illumination. EDXRF enables detection existence and quantity of elements in the sample.

A conventional EDXRF inspection system typically includes an X-ray source configured to emit X-ray radiation, a suitable optical system selected to focus the X-ray radiation onto a selected inspection spot, and an X-ray detector configured to collect photons emitted from the sample in response to illumination by X-ray radiation. The photons emitted by the sample typically include a mixture of X-ray radiation components emitted by fluorescent response of different atoms (elements) in the sample as well as elastically and in-elastically scattered photons. The design and operation of X-ray fluorescent (XRF) detectors are well known in the art and hence will not be discussed herein. Generally described, the x-ray detector resolves one or more x-ray photon energies from the collected photons and outputs a first measurement data formed of electric signals indicative of x-ray energy components. The energies of the collected photons are indicative of properties of the sample. The detector may transmit output data to a controller for processing the detected photons' energies and provide output data on material composition of the sample.

Thus, as indicated above, each of the first 12 and second 14 inspection units include at least an X-ray radiation source, suitable optical elements for directing X-ray radiation onto a selected inspection spot on the sample, and one or more detectors. In some embodiments, each the first 12 and second 14 inspection units includes an arrangement of two, three, or four detectors positioned at selected angles for collecting radiation emitted from the sample.

Generally, according to the present disclosure, the first 12 and second 14 inspection units include one or more inspection unit including a monochromatic X-ray inspection unit. Such monochromatic X-ray inspection unit is generally configured to emit X-ray radiation of one or more selected, relatively narrow, energy bands (corresponding to one or more wavelength ranges). For example, in some embodiments the first inspection unit 12 may utilize a monochromatic X-ray inspection unit and the second inspection unit 14 may utilize a polychromatic X-ray inspection unit, operable to emit a relatively broadband of X-ray radiation frequencies. In some other examples, the first 12 and second 14 may both utilize monochromatic X-ray inspection units, operable with respective first and second X-ray wavelength ranges, different between them, and/or first and second different focusing power providing illumination spots of first and second different diameters.

In this connection, a typical monochromatic X-ray inspection unit may operate to provide illumination using one or more discrete energy bands of radiation. Such monochromatic inspection unit may operate to emit radiation within a single, relatively narrow energy band, or within two or three relatively narrow energy bands that are non-overlapping between them. The monochromatic inspection unit may utilize monochromatic X-ray source. Alternatively, the monochromatic X-ray inspection unit may utilize a polychromatic X-ray source and an optical arrangement configured to filter radiation emitted from the X-ray source, to generate radiation of one or more discrete energy bands. For example, the monochromatic X-ray inspection unit 12 may utilize an optical arrangement including one or more multilayer optical elements having layered configuration selected to provide predetermined band-pass filtering to X-ray radiation directed thereon, thereby allowing radiation of one or more selected discrete energy bands to be directed at the sample.

Generally, the use of first and second inspection units, operable using respective first and second different X-ray frequency ranges, enables adjustment of sample inspection to detect selected groups of elements that may be present within the samples. For example, the use of typical broadband X-ray source enables high photon flow and allows efficient detection of high quantities of various elements. However, the use of broadband X-ray illumination may generate large number of scattered photons (by elastic or in-elastic scattering) that can mask the fluorescent photons generated due fluorescent response from certain elements existing in low quantities/concentrations. On the other hand, inspection using a narrow-band X-ray illumination enables high spatial resolution of inspection and allows for efficient detection of elements that exist in the sample in low concentrations, with increased signal to noise ratio. For example, this may be advantageous for detection of low concentration levels of Silver (Ag) in AgSn bumps, where the use of specific and narrow energy bands for inspection reduces undesired scattering and enhances signal to noise ratio. Similarly, the use of first and second monochromatic X-ray inspection units, operable with respective first and second different energy bands (wavelength ranges), and/or first and second different illumination spot characteristics (diameter, shape), enables tailoring of sample inspection for detection of selected groups of elements to provide high resolution inspection.

Accordingly, the use of at least first 12 and second 14 inspection units, configured with respective first and second different X-ray illumination properties, enables enhancement of sample inspection accuracy and robustness, while maintaining a generally similar form factor of the inspection system. As sample inspection may generally take place within a clean room, the present technique enables for increasing inspection output per unit area of the clean room and allows for additional and more sensitive inspection within a given clean room infrastructure.

Figure 2:
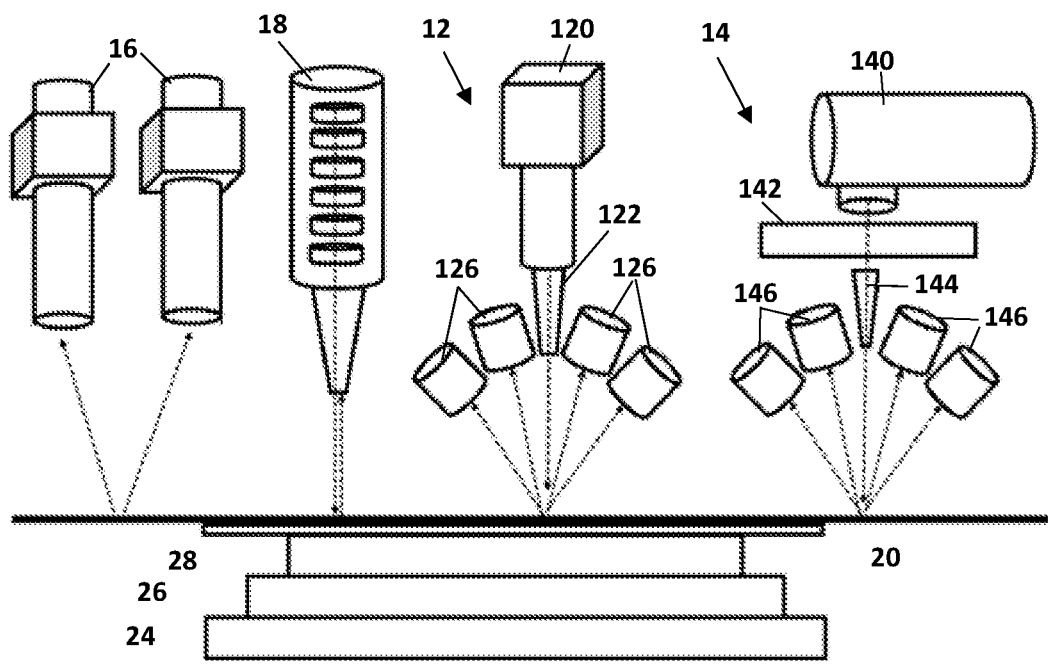
FIG. 2 exemplifies inspection units arrangement according to some embodiments of the present disclosure.

In this connection, FIG. 2 exemplifies a specific and non-limiting arrangement of the at least first 12 and second 14 inspection units in an inspection system 100 according to some embodiments of the present disclosure. FIG. 2 illustrates an arrangement of units of the system, while for simplicity, FIG. 2 does not specifically show mounting arrangement including the at least one horizontal beam on which the inspection units are mounted. The arrangement of units may additionally include two-dimensional microscopes 16 and three-dimensional scanner 18, both configured to provide optical inspection of the sample using visible to test and measure locations for inspection on the sample. The system further includes a sample mount 20 positioned on moveable stage including height adjustment 28, Y-axis adjustment 26 and X-axis adjustment 24, configured to enable selective translation of the sample in accordance with instructions provided from a computer system or operator.

In this exemplary embodiment, the first inspection unit 12 is configured as a monochromatic X-ray inspection unit, using an X-ray source 120 configured to emit X-ray radiation of a selected wavelength range and an optical arrangement 122. The monochromatic inspection unit generally includes one or more filtering elements configured to provide band-pass filtering. This provides illumination of one or more energy bands having bandwidth of up to 2 KeV, or up to 1 KeV or up to 500 eV, and being separated between them. The optical arrangement 122 includes one or more optical elements for focusing emitted radiation onto a selected spot size on the sample. Additionally, inspection unit 12 includes an arrangement of detectors 126. Generally, the one or more filters may be associated with one or more multilayer optical elements of the optical arrangement 122, or be formed by separate filters associated with the X-ray source 120.

Monochromatic illumination by the monochromatic inspection unit 12 is generally characterized by one or more discrete energy bands of X-ray radiation impinging onto the sample. Typically, the X-ray source 120 may generate a relatively broadband emission, and the optical arrangement 122 includes one or more multilayer optical elements providing band-pass filtering of the emitted radiation. The one or more multilayer optical elements may be configured as dichroic optical elements and/or Bragg filters, configured to allow transmission (or reflection) of selected one or more energy bands of X-ray radiation. Accordingly, the monochromatic inspection unit 12 is configured to provide illumination using one or more (e.g., one, two or three) discrete and non-overlapping, energy bands, each having a relatively narrow bandwidth being generally up to 2 KeV, or up to 1 KeV, or preferably up to 500 eV.

In some embodiments, the monochromatic inspection unit 12 may include a generally monochromatic X-ray radiation source 120, configured to provide emission of X-ray radiation having one or more discrete and non-overlapping, energy bands, each having a relatively narrow bandwidth. This may be achieved by one or more filters placed within the X-ray radiation source 120 rather than in the optical arrangement 122 thereof.

Further, in this exemplary embodiment, the second inspection unit 14 utilizes a broadband X-ray illumination spectrum. To this end, the second inspection unit 14 may utilize an X-ray emission tube 140 configured to emit large spectrum of X-ray frequencies, an X-ray filter 142, an optical arrangement 144 (e.g., polycarpellary optical arrangement) for focusing the emitted X-ray illumination onto an illumination spot on the sample, and an arrangement of detectors 146.

Each of the first 12 and second 14 inspection units is associated with a specific, preselected, position of the illumination spot. Location of the first and second illumination spots are typically characterized by selected coordinates of stage 20 location, enabling directing the sample to a selected first coordinate position for inspection using the first inspection unit 12, and further translating the sample to a second coordinate position for inspection using the second inspection unit 14.

Also exemplified in FIG. 2 are optical inspection units (microscopes) 16 and 18. In this example, the system may utilize one or more two-dimensional microscopes 16, and a three-dimensional scanner 18. Generally, the system may include first and second optical inspection unit 16 and 18 configured to provide optical inspection of the sample using first and second different focal lengths respectively. Accordingly, the different microscopes may provide at least two different magnification ratios and fields of view of the sample. Each of the optical microscopes is positioned for imaging of a sample at a selected stage position based on prestored coordinates, enabling optical inspection of the sample with selected optical and magnification condition by translation of the sample. This configuration allows for varying field of view, magnification and other optical conditions for imaging while avoiding the need for shifting optical elements above the sample. Typically, movement of various elements above a sample within the system may release particles that may contaminate the sample. Accordingly, the use of at least first and second optical microscopes combined within the inspection system 100 enables improved optical inspection while reducing possible contamination of inspected samples.

Figure 3A:
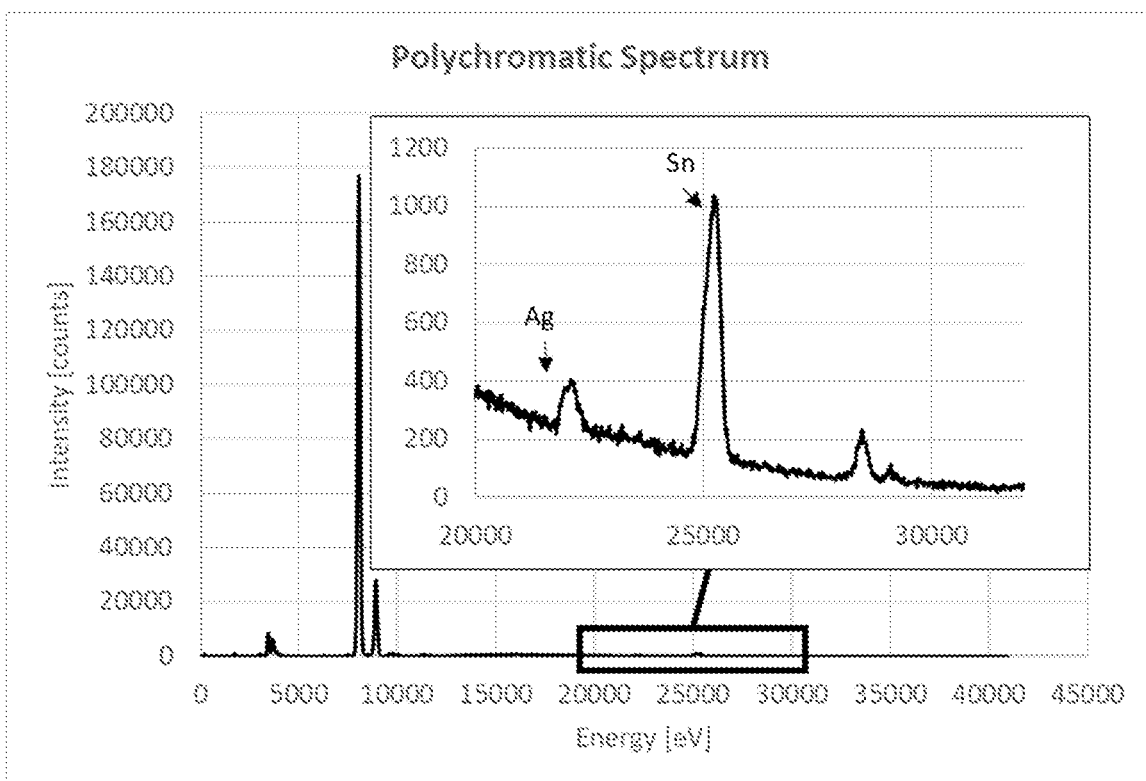
FIGS. 3A and 3B exemplify inspection sensitivity between polychromatic X-ray inspection (FIG. 3A) and monochromatic X-ray inspection (FIG. 3B) for detection of certain elements according to some embodiments of the present disclosure.
Figure 3B:
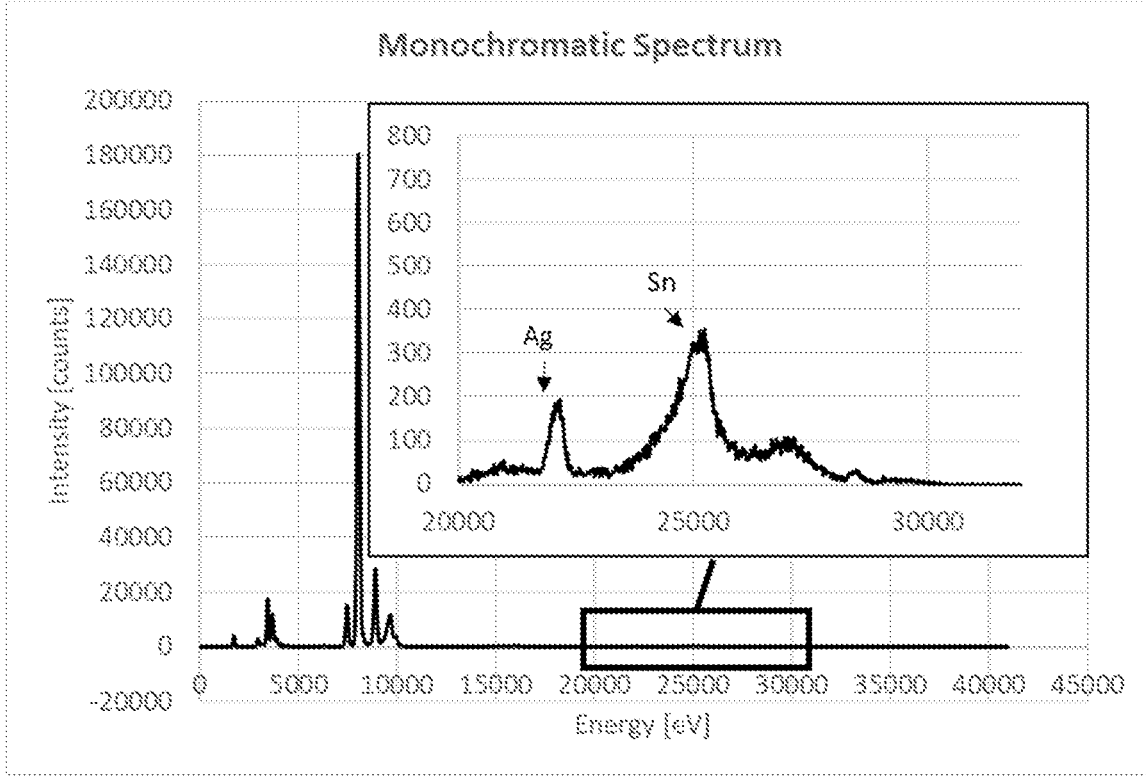

The exemplary configuration illustrated in FIG. 2 above may provide various advantages for elemental inspection of a sample. As indicated above, the use of at least first and second X-ray inspection unit may enable enhanced inspection of samples. FIGS. 3A and 3B showing detection spectrum associated with some elements to be detected in a sample. FIG. 3A shows detection spectrum on AgSn sample collected using a polychromatic X-ray inspection system, and FIG. 3B shows detection spectrum of the same sample collected using a monochromatic X-ray inspection system having bandwidth of 500 eV. As shown in both figures, the Ag signal is generally low with respect to various other elements in the sample including Sn. In FIG. 3A the background radiation around the peak associated with Ag is relatively high and may reduce sensitivity to variations in Ag amount, or may hide the peak completely. The use of monochromatic X-ray inspection system reduces the background radiation as shown in FIG. 3B, allowing enhanced sensitivity in detection of the Ag peak, or peaks associated with other elements that exist in the sample in low amounts. This is while the Sn peak is clearly visible when detected in both inspection systems due to the high amount of SN atoms in the sample.

It should be further noted that the present disclosure provides an inspection system utilizing at least first and second X-ray inspection units. The above example of FIG. 2 illustrates a system utilizing a polychromatic inspection unit 14 and a monochromatic inspection unit 12. In this connection it should be noted that the system according to some embodiments of the present disclosure may utilize first and second monochromatic inspection units, operable as first 12 and second 14 inspection units of the system 100. In such configuration, the at least first 12 and second 14 monochromatic inspection units may operate with respective first and second different wavelength ranges, and/or respective first and second X-ray beam power. This configuration enables broad band of inspection with reduced noise for selected wavelengths, while eliminated the need for shifting elements above the sample, thereby reducing any contamination of the sample. Further as indicated above, the inspection system of the present disclosure enables a generally similar form factor to typical inspection system, while providing two or more different inspection techniques.

Further, different inspection unit, and selected optical elements and operation parameters for the inspection units 12 and 14 provide selected inspection properties. For example, the use of polycapillary optical arrangement 144 combined with polychromatic X-ray source 140 as exemplified in FIG. 2, can provide a relatively high photon flux, while the monochromatic inspection unit 12 operated with narrowed beam to provide reduced background noise and may be useful for detection of selected predefined elements. This enables fast scanning of a sample using the polychromatic inspection unit 14 and marking of selected region that may require additional inspection for selected elements, for which the monochromatic inspection unit 12 may be more suitable. Further, the sue of selected different optical elements for the first 12 and second 14 inspection unit may enable tailoring of selected scanning parameters, allowing a direct scan of a sample while reducing potential contamination by avoiding any moving elements over the sample. For example, selection of wider scanning beam increases scan speed but may cost in scan resolution and sensitivity to small concentration of elements. The use of additional, monochromatic inspection unit enables providing narrower scan beam at selected wavelength range to provide accurate data on small features of the sample and elements are present in low concentrations.

Accordingly, the selected inspection units may include monochromatic and polychromatic X-ray inspection units, two monochromatic X-ray inspection units operating at different X-ray energies (wavelengths), or operating with different optical properties (e.g., illumination spot size), or two polychromatic X-ray inspection unit operating with different optical properties such as spot size. While polychromatic and monochromatic X-ray inspection units may utilize similar spot size. It is advantageous according to the technique of the present disclosure that spot size of the first and second inspection unit is different, to enable improved scanning and inspection efficiency.

Figure 4A:
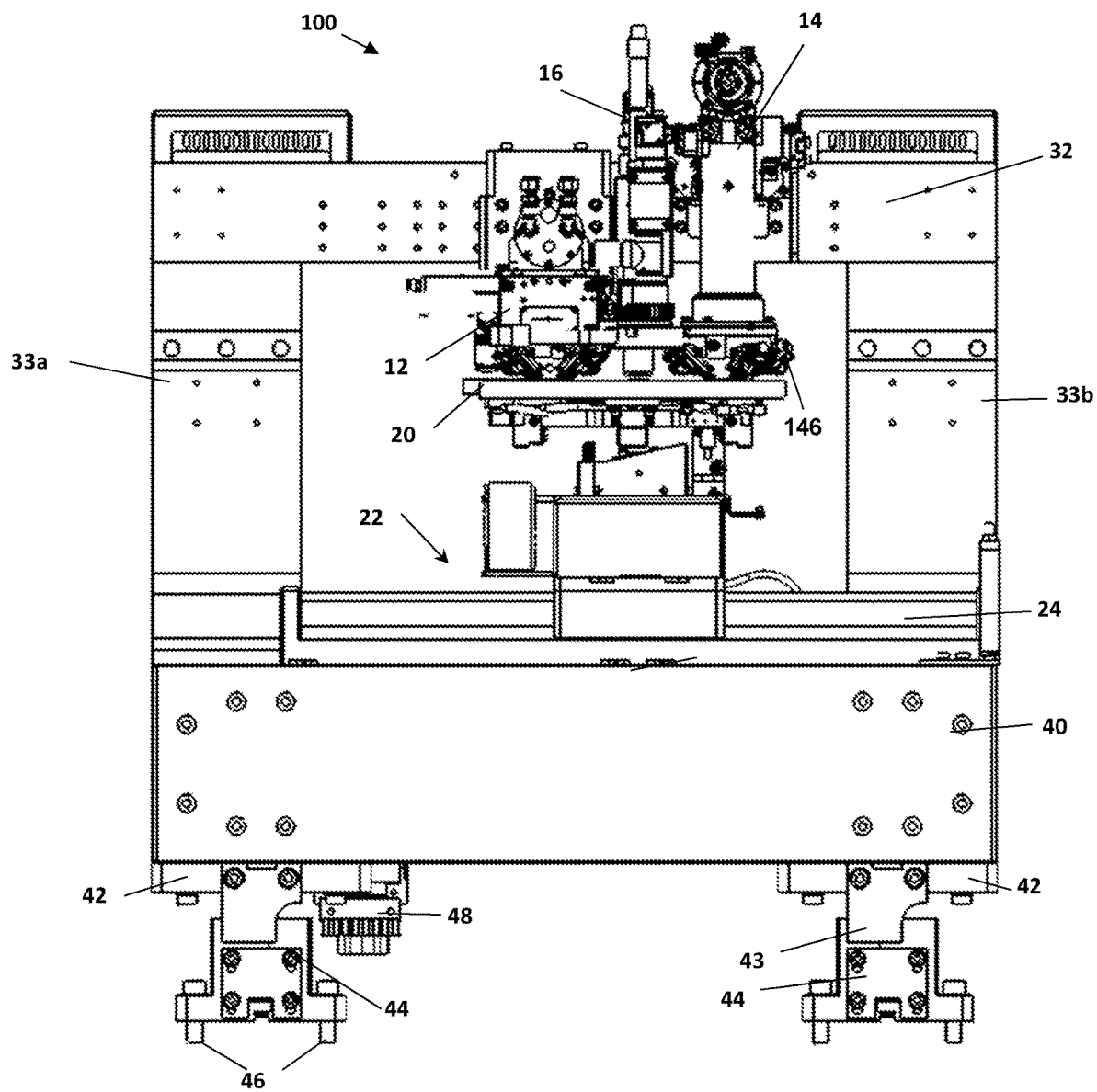
FIGS. 4A and 4B illustrate front (FIG. 4A) and side (FIG. 4B) views of an inspection system and a mounting arrangement of inspection units according to some embodiments of the present disclosure.
Figure 4B:
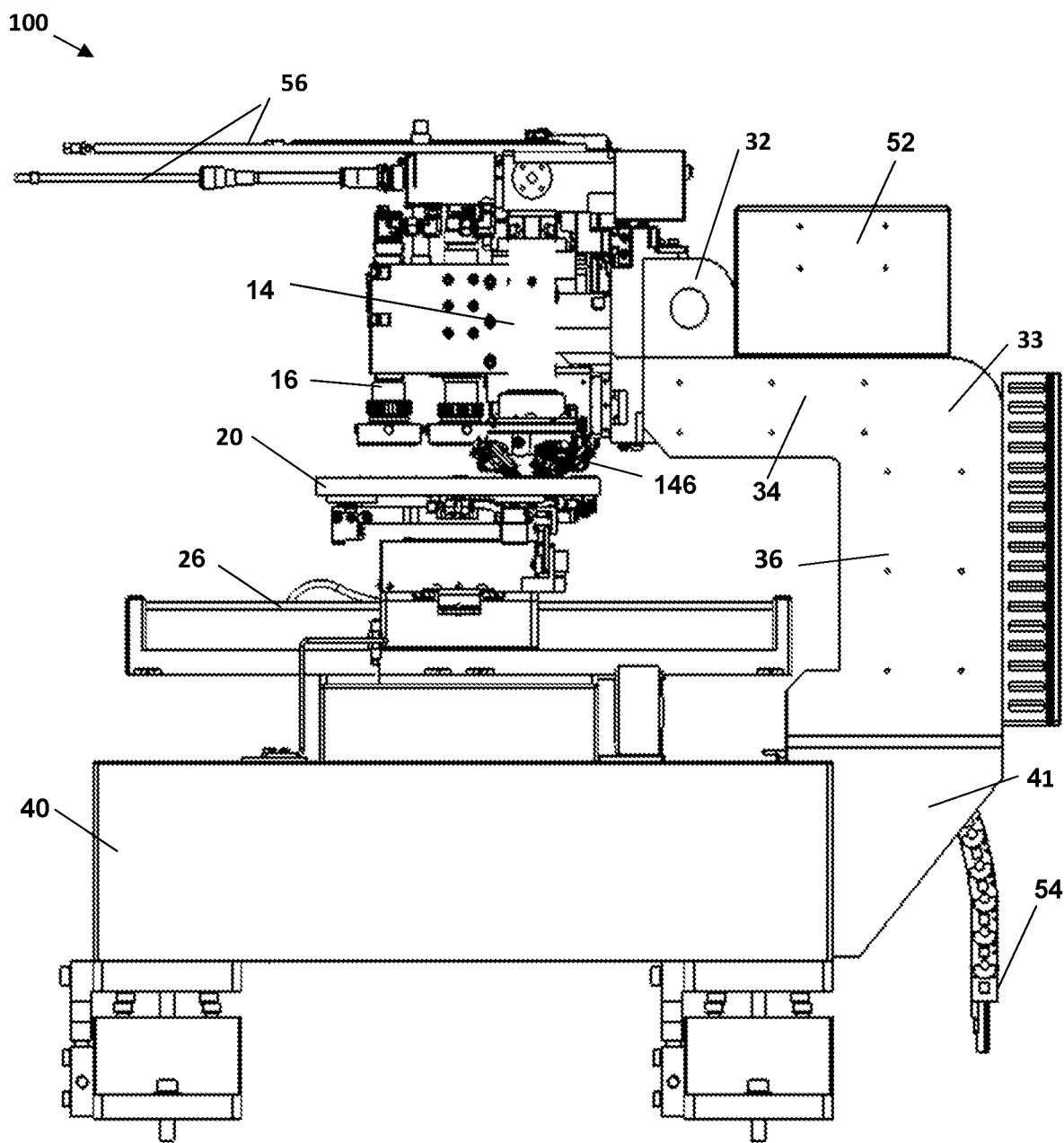

FIGS. 4A and 4B show another exemplary illustration of system 100 according to some embodiments of the present disclosure. FIG. 4A shows a front view of the system 100 and FIG. 4B shows a side view of the system 100. As illustrated, the first 12 and second 14 inspection units and its respective detectors 146, as well as at least one optical microscope 16 are mounted on a common mounting arrangement. The mounting arrangement is formed of a horizontal beam 32 positioned above the sample region 22. Typically, the horizontal beam 32 is shifted laterally from center of the sample region 22 to position the inspection units is a relatively central position.

The horizontal beam 32 is supported by at least two support beams 33a and 33b located at different sides of the sample region 22. The horizontal beam 32 and the two support beams 33a and 33b may be made of high strength material such as granite, steel, ceramic materials, strengthen concreate, or other selected materials. The support beams 33a and 33b and the horizontal beam 32 are mounted of frame of the system and may be directly mounted on the ground to provide stability and reduce vibrations and flexibility of the structure given weight of two or more inspection units mounted on the horizontal beam 32.

In some embodiments, the support beams 33a and 33b may have an inverted "L" shape. More specifically, the support beams may include a first vertical portion stretching from bottom end of the system (e.g., positioned on the floor or on stable frame of the system) and extending upward to a selected height. The first vertical beams are located at two corners of the system outside the sample region 22. At the selected height, horizontal support beams extend from the first vertical support beams above the sample region. The horizontal support beams support the main horizontal beam 32 and place the horizontal beam 32 above the sample region 22 while providing easy access to the sample region 22 for placing and removing samples for inspection.

Also illustrated in FIG. 4A is the base arrangement of system 100, the support beams 33a and 33b are positioned and connected to a base structure 40. Base structure 40 may form main chassis element of the system and may be made of selected high weight high density material such as granite. Base structure 40 provides for lowering center of mass of the system and reducing transmission of environmental vibrations to the system. To this end, base structure 40 is placed on a selected surface mounted on vibration filtering legs. In this example, base structure is placed on and connected to connection unit 42, which is mounted on the system legs 44 using vibration damping connections 43. Further system legs 44 may preferably be connected to the ground using attachment screws 46.

Referring to FIG. 4B, the support beams 33a and 33b are better illustrated showing the inverted "L" shape thereof. More specifically, the support beams 33 include a first vertical support beam 36 mounted on corners of the base structure 40, e.g., using corner connection unit 41, and stretch upward to a selected height "h", and a second horizontal beam portion 34 extending from the vertical beam 36 toward center of the sample region. The vertical 36 and horizontal 34 beam portions may preferably form a single unit having a corner shape. In some embodiments however, the support beams 34 and 36 may be formed of two separate beams connected between them.

Also shown in the side view of FIG. 4B are control box 52, including cable arrangement and controllers for the first and second inspection units 12 and 14 and the optical microscope(s) 16, cable arrangement 54 typically extending from the control box 52 along the support beams 33 and out of the system 100 to connect to power grid, one or more computer systems etc. further, also shown are X-ray source connectors 56 configured to provide gas and power to the X-ray sources of the first and second inspection units 12 and 14.

The inspection system chassis may enable installing of selected arrangement of first and second inspection units and corresponding optical microscopes. To this end the system 100 may include a system chassis formed of at least the chassis base 40, support beams 33a and 33b and horizontal beam 32. The sample stage 20 and translation units 22 to 26 may be placed on the chassis base 40. Additionally, the chassis system may include an enclosure (not specifically shown) allowing inspection operation within a clean room, while eliminating X-ray radiation emission outside of the system enclosure. The horizontal beam 32 may be formed with a plurality of mounting positions, e.g., in the form of screw holes, for attachment of the selected inspection units. Generally, the horizontal beam 32 may include a selected arrangement of attachment points for mounting the at least first and second x-ray inspection units. The attachment points may be arranged on at least two of top, side, and bottom surfaces of said horizontal beam to enable connecting the one or more connectors onto two or more surfaces of the horizontal beam 32.

The first and second inspection units 12 and 14, optical microscope(s) 16, or any additional unit, may be mounted on the horizontal beam via respective connectors. The connectors are formed with a first end configured for mounting on the horizontal beam, and a second end configured for connecting to the respective inspection unit or microscope. In this connection, reference is made to FIGS. 5A to 5D and FIGS. 6A to 6D illustrating connectors of the first and second inspection units.

Figure 5A:
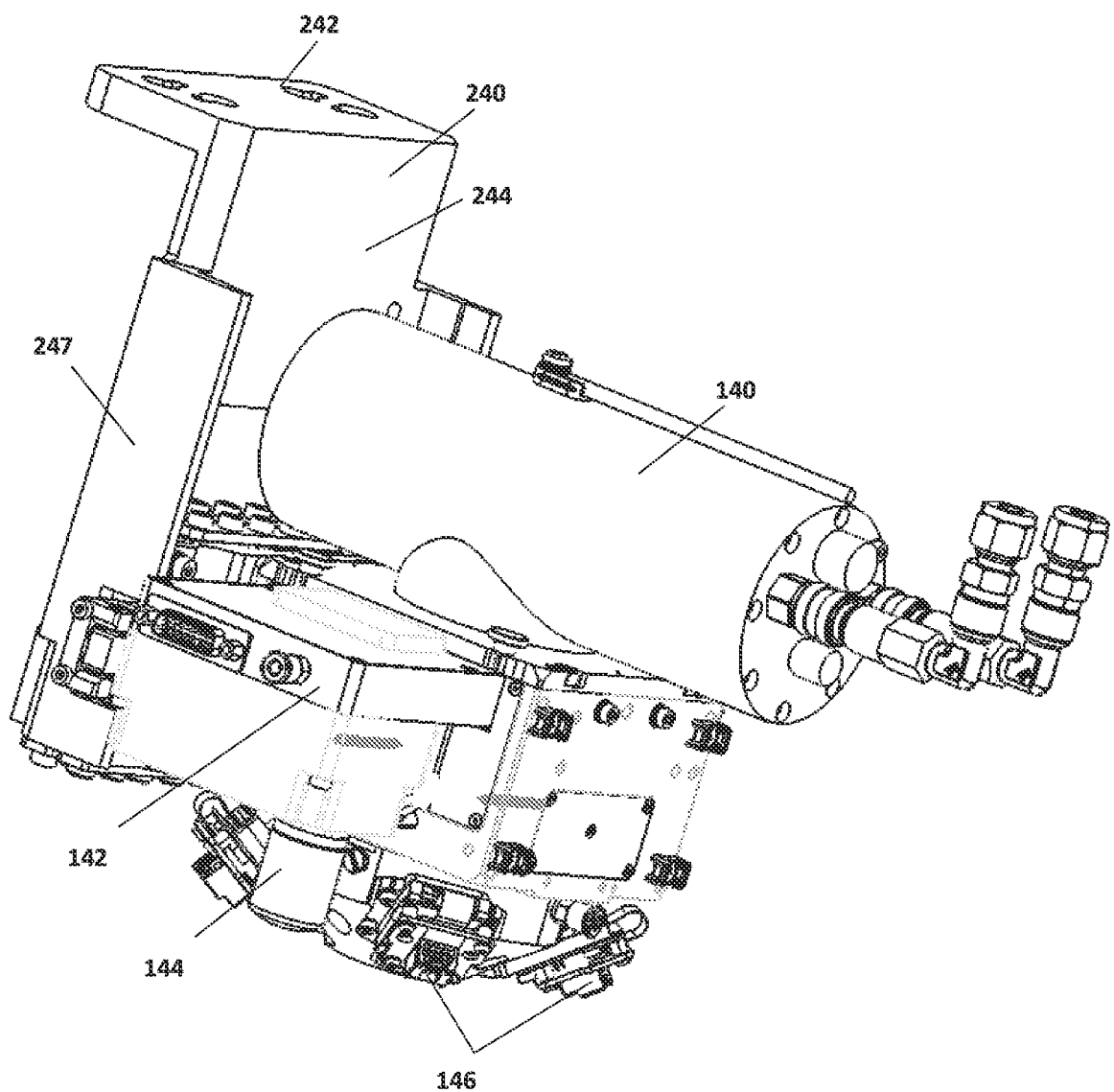
FIGS. 5A to 5D show an inspection unit and respective one type of connector, including different perspectives and an exploded view according to some embodiments of the present disclosure.

FIG. 5A illustrates a second inspection unit 14 including a polychromatic X-ray source 140, filter 142, polycapillary optical arrangement 144 and an arrangement of one or more detectors 146. The inspection unit 14 is mounted on a connector 240 configured for mounting on the horizontal beam according to some embodiments of the present disclosure. The connector 240 illustrated from this specific perspective is shown to include a main plate 244, top portion 242, and front side portions 247.

Figure 5B:
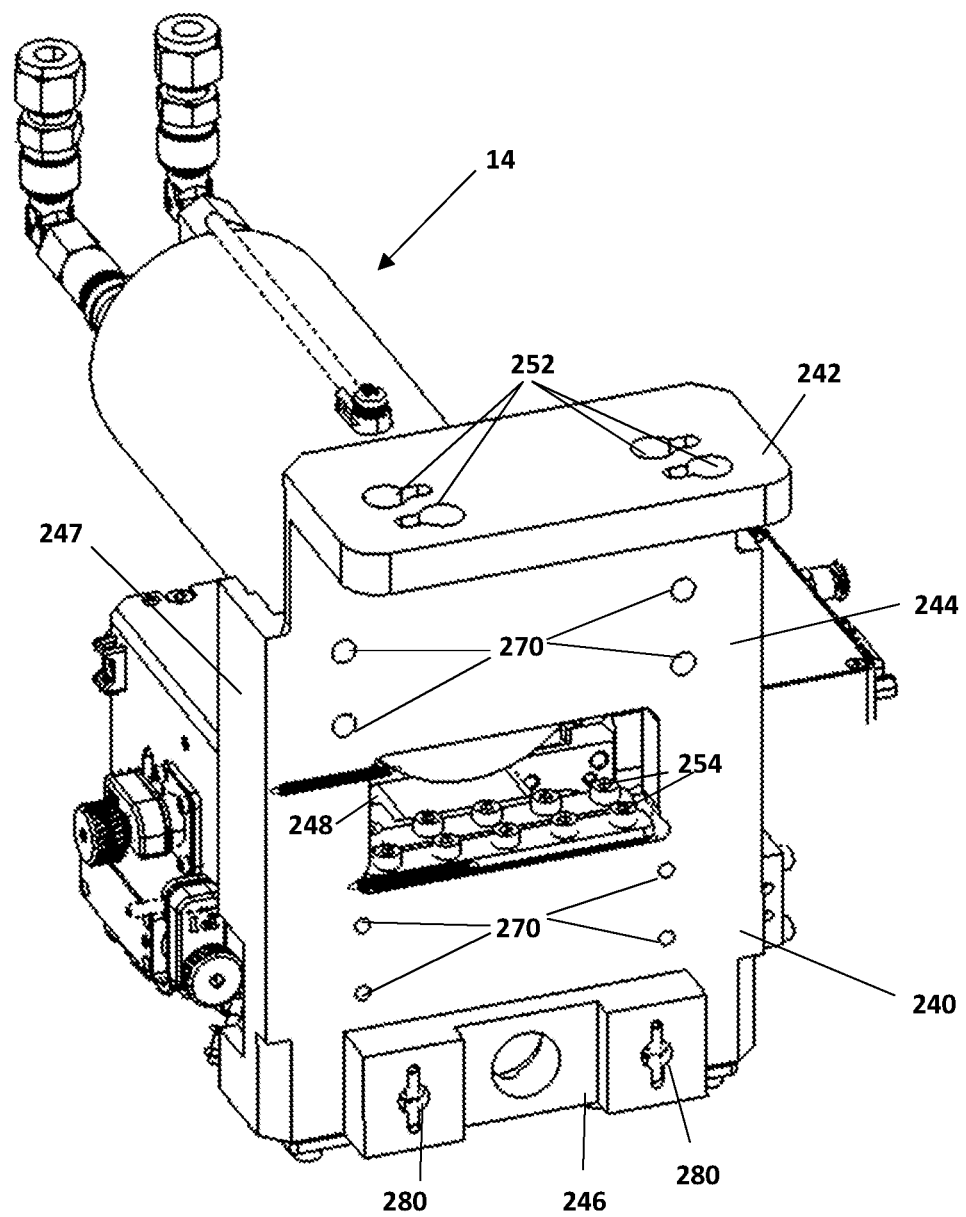

FIG. 5B shows another perspective of the second inspection unit 14 and respective connector 240, viewed from perspective of the horizontal beam 32. As shown, the connector 240 includes a main plate 244 having a groove 248, top portion 242, bottom portion 246 and front side portions 247. Also shown are a set of connecting bolts (e.g., screws) 254 connecting the inspection unit 14 to the connector 240. The set of connecting bolts 254 are shown here connecting the inspecting unit 14 to a surface formed in the groove 248, providing easy access when the inspection unit is detached from the horizontal beam 32. The top portion includes an arrangement of connection holes 252, generally suitable for sliding in onto a selected number of connecting bolts, or mounting using connecting bolts after placing the connector 240 in place on the horizontal beam 32. Also shown in FIG. 5B are grooves 270 located on the beam facing side of main plate 244 and spring locks 280 placed on bottom portion 246.

Figure 5C:
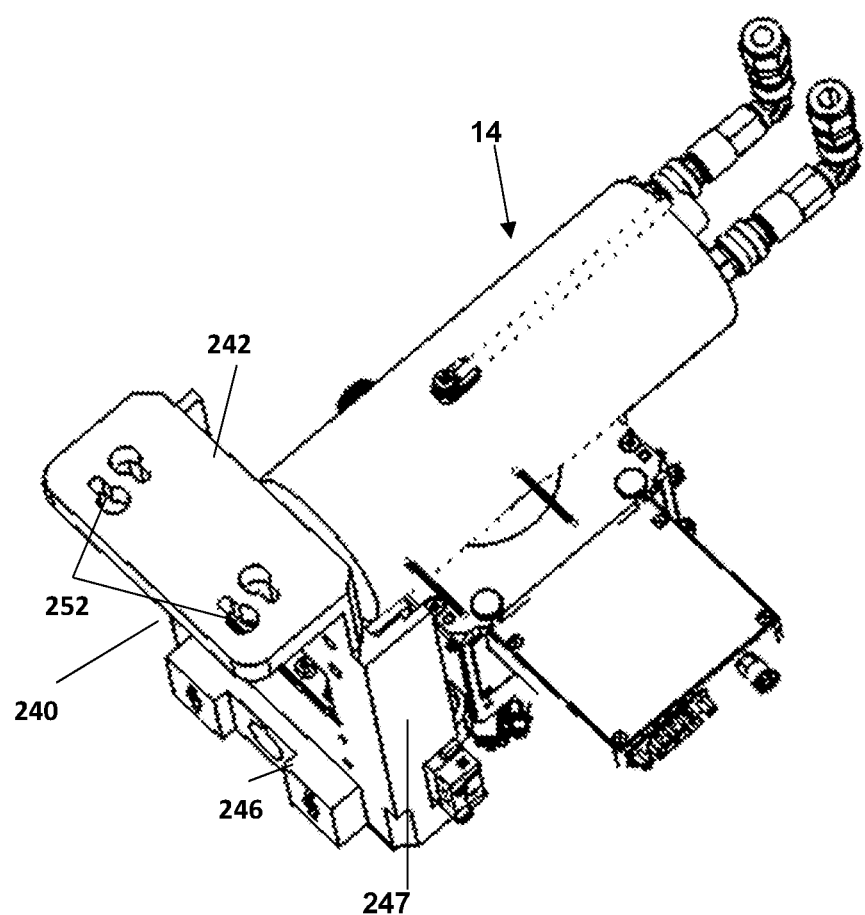
Figure 5D:
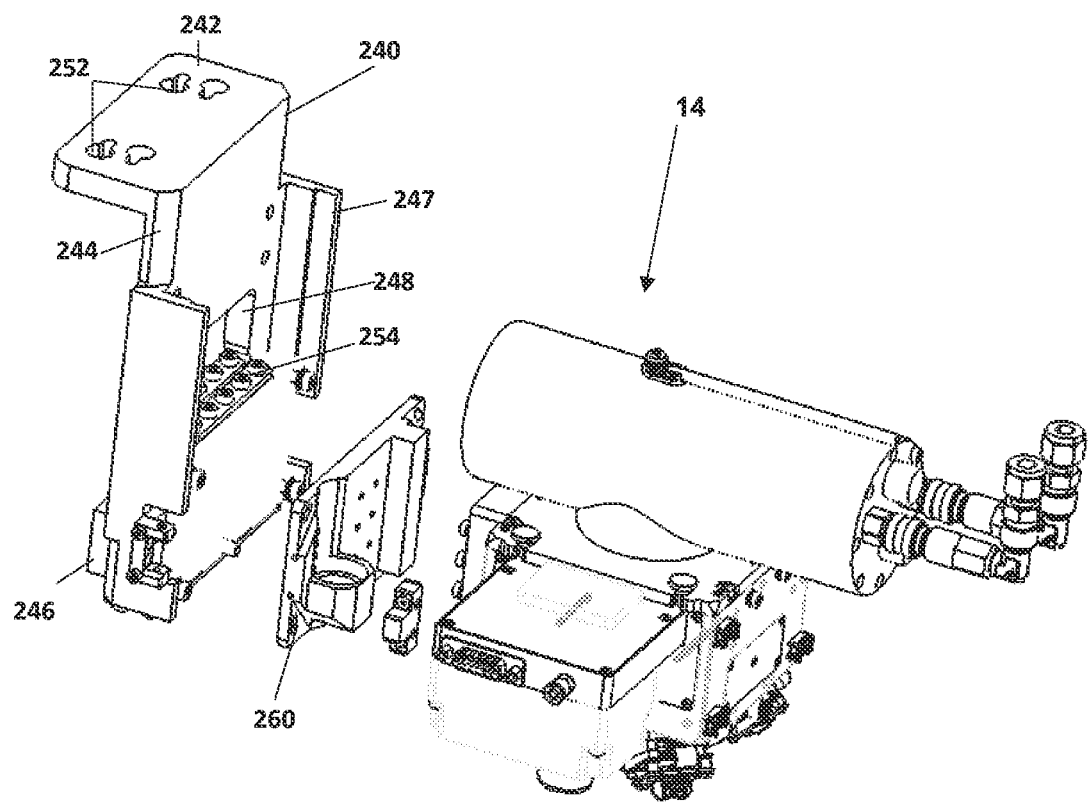

FIG. 5C shows a top view of the inspection unit 14 mounted on connector 240. This figure shows the top portion 242 and respective connection holes 252, side portion 247 and bottom portion 246. FIG. 5D shows an exploded view illustrating the inspection unit 14, dedicated inspection unit mount side 260 and connector 240, separated between them, as well as further elements illustrated in FIGS. 5A to 5C.

Figure 6A:
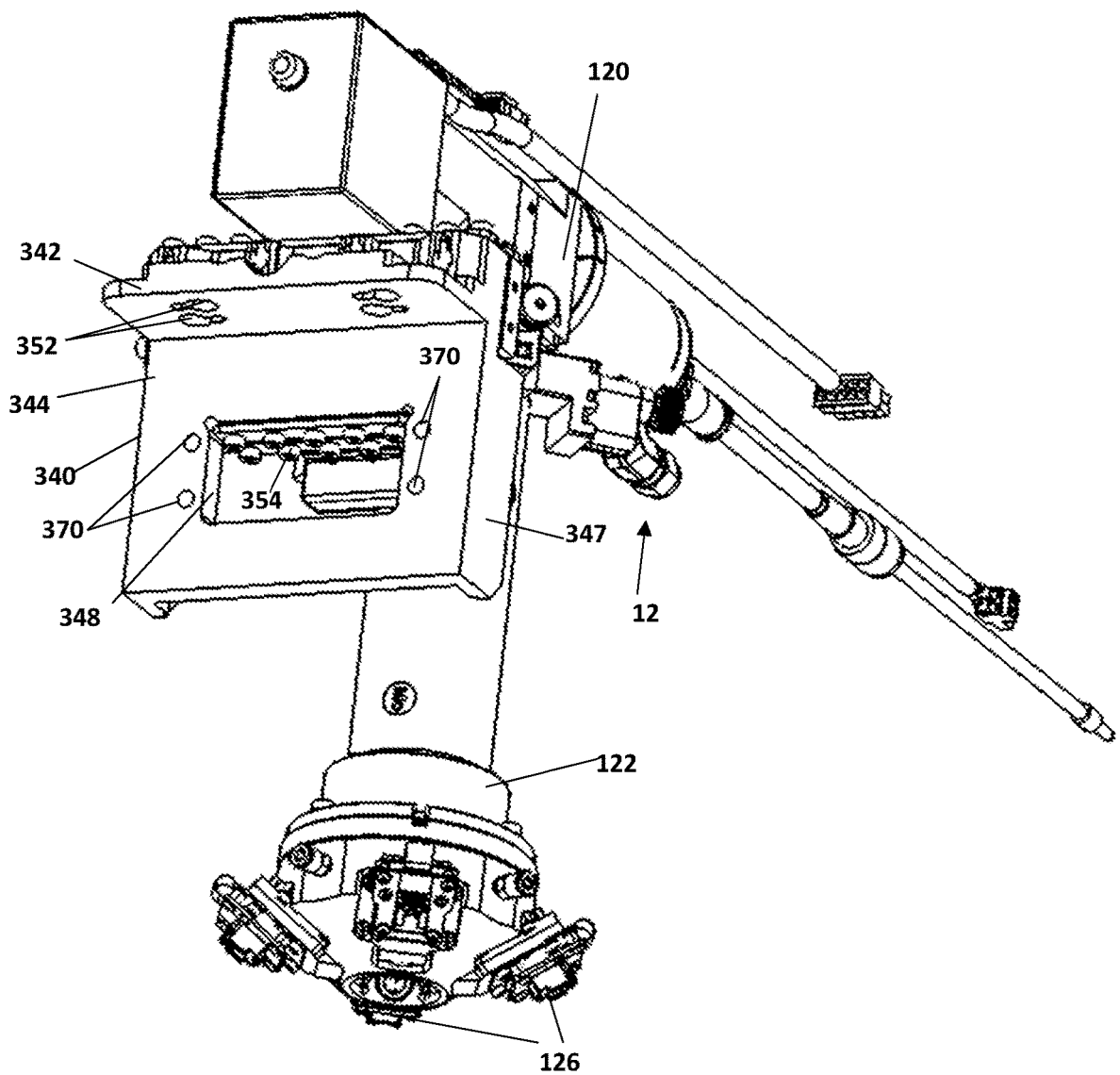
FIGS. 6A to 6D show another inspection unit and respective one type of connector, including different perspectives and an exploded view according to some embodiments of the present disclosure.

FIG. 6A illustrates a first inspection unit 12 mounted on a corresponding connector 340. In this example, the first inspection unit 12 utilizes an X-ray source 120, optical arrangement 122 and a set of detectors 126 and is configured to provide illumination with one or more discrete (and generally non-overlapping) energy bands of X-ray illumination. Connector 340 is exemplified including main plate 344, top portion 342, side portions 347, and main plate aperture 348. The top portion includes specific hole arrangement 352 generally similar to the top portion 242 of connector 240. In this example, the inspection unit is connected to the connector 340 using bolts 352 at a tope surface of the aperture 348.

Figure 6B:
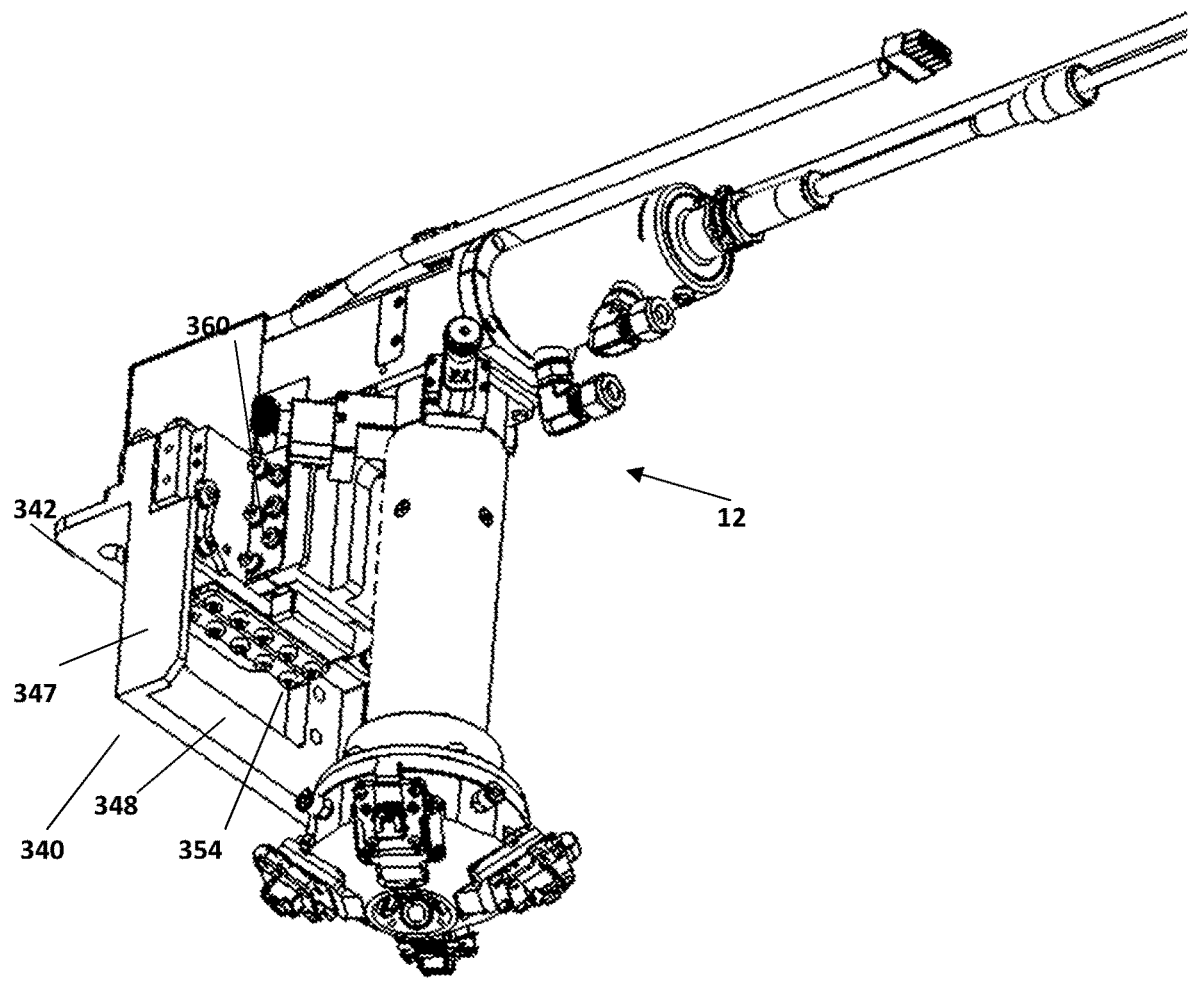
Figure 6C:
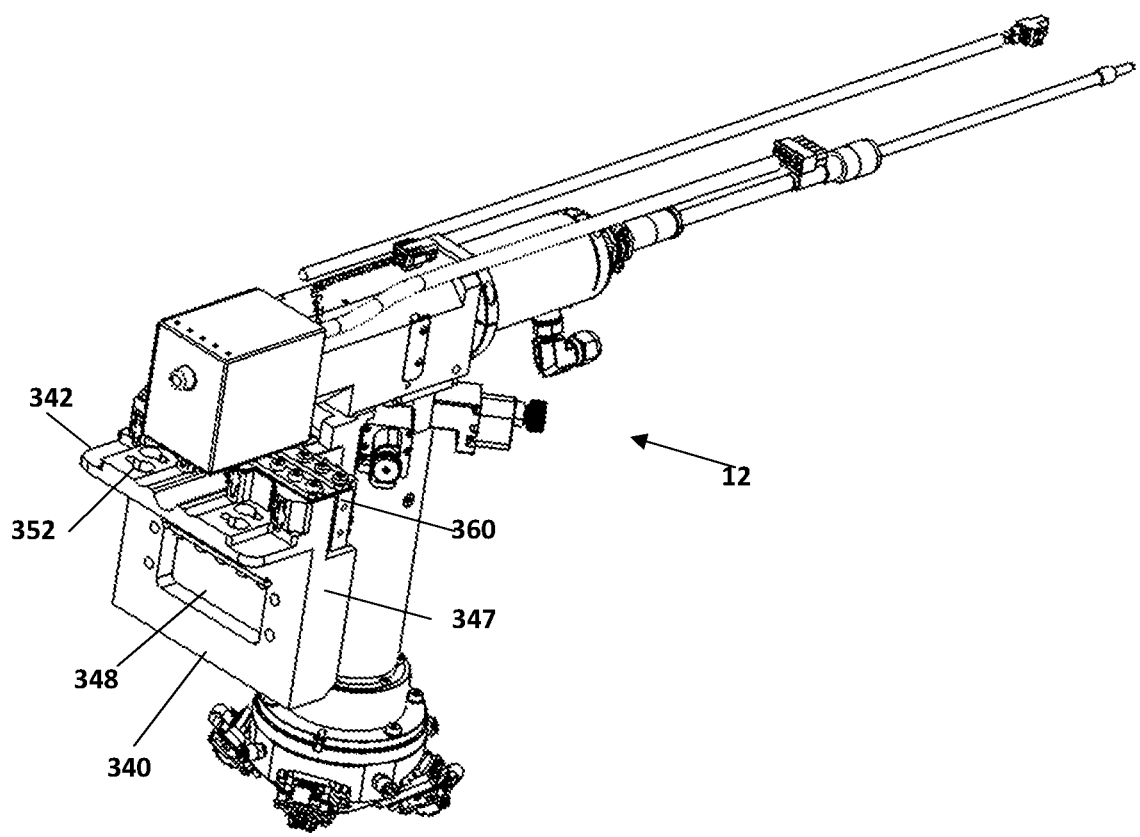
Figure 6D:
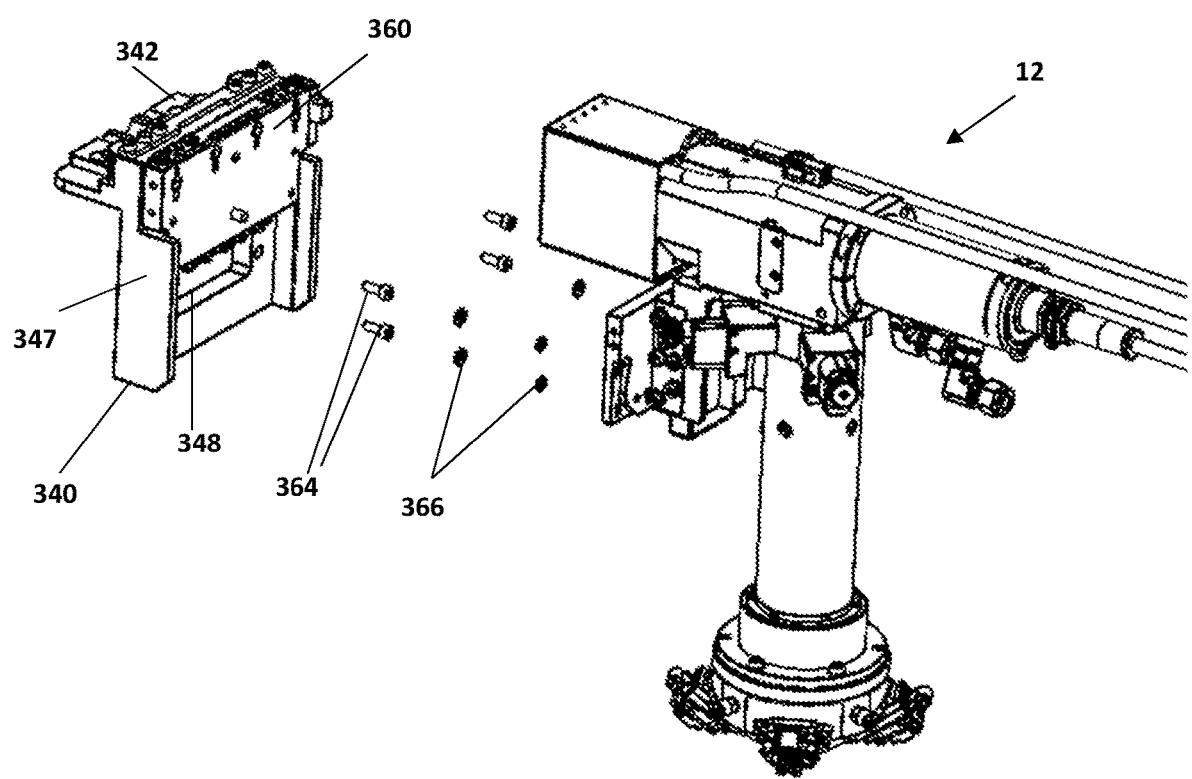

FIGS. 6B and 6C show the first inspection unit 12 and corresponding connector 340 from additional perspectives. FIG. 6D shows an exploded view of the inspection unit 12 and the connector 340. The inspection unit 12 may be connected using bolts 364 and washers 366 to the connection plate 360, which in turn may be connected to the connector 340 using bolts 352. The connector may also include an arrangement of groves 370 located on beam side of the main plate 344.

Generally, the horizontal plate 32 of the system 100 according to the present disclosure may be configured to enable mounting of the first and second inspection units at several selected, and interchangeable locations. The horizontal beam 32 may be configured to drilled holes for bolts on top, bottom, and side thereof, in selected and generally repeating pattern. The connector 240 or 340 are configured with main plate 244, 344 to be facing a vertical wall along side of horizontal beam 32 and top portion 242, 342 configured for mounting on top side of the horizontal beam. In some embodiments, as exemplified in FIGS. 5A to 5D and 6A to 6D, the connectors may include grooves or bolt holes 270, 370 of the main plate 244, 344 for securely placing the connector at selected positioned along the horizontal beam 32.

Grooves 270, 370 may be formed as small notches extending outward from main plate 244, 344, or inward with respect to surface of main plate 244, 344. The grooves 270, 370 are preferably configured in accordance with corresponding opposite grooves on vertical wall of the horizontal beam 32, to properly position the connectors. In some embodiments, groove 270, 370 may be formed as holes suitable for connecting using one or more bolts to horizontal beam.

Generally however, the connectors 240, 340 may be securely connected to horizontal beam 32 using one or more bolts on top portion of the connectors 242, 342. The top portion 242, 342 is generally placed on top side of the horizontal beam, and includes an arrangement of holes 252, 352 for selected number of bolts to secure the connector 240, 340 in place. In some embodiments, or some connectors as illustrated in FIGS. 5A to 5D, the connectors may also include a bottom portion 246 including a spring locking mechanism enabling further attachment of the connector to the horizontal beam 32.

Generally, the connectors 240, 340 and configuration of the first and second inspection units and the horizontal beam carrying the inspection units, is configured to provide simple installment, while holding the inspection units 12, 14 at stationary position within the system. Such stationary position enables repeatability in scanning of different samples, as field of view and illumination spot location of each of the inspection units 12, 14 is fixed in space. Further, maintaining the inspection units 12, 14 and optical microscope(s) 16 stationary during inspection, and obviating the need for any moving elements during inspection, eliminates, or at least significantly reduces sample contamination due to release of particles such as oil particles within the inspection system.

Accordingly, as indicated above, the present disclosure provides an inspection system configured for operating with two or more inspection units, generally configured for X-ray inspection of samples. The use of two or more inspection units operable with respective two or more different inspection properties (such as emission bandwidth, emission energy range, illumination spot size, etc.) enables to provide complete inspection of various samples, where one inspection unit performed wide range inspection for (i) large field of view, or (ii) strong elemental signals based on high concentration, and another inspection unit is directed at (i) pin pointing smaller spot size, or (ii) accurate wavelength range for inspection of low concentration elements. The present technique thus enables saving of high value clean room area, and operation time, providing generally complete inspection of complex samples within form factor of a single inspection system.

Figure 7:
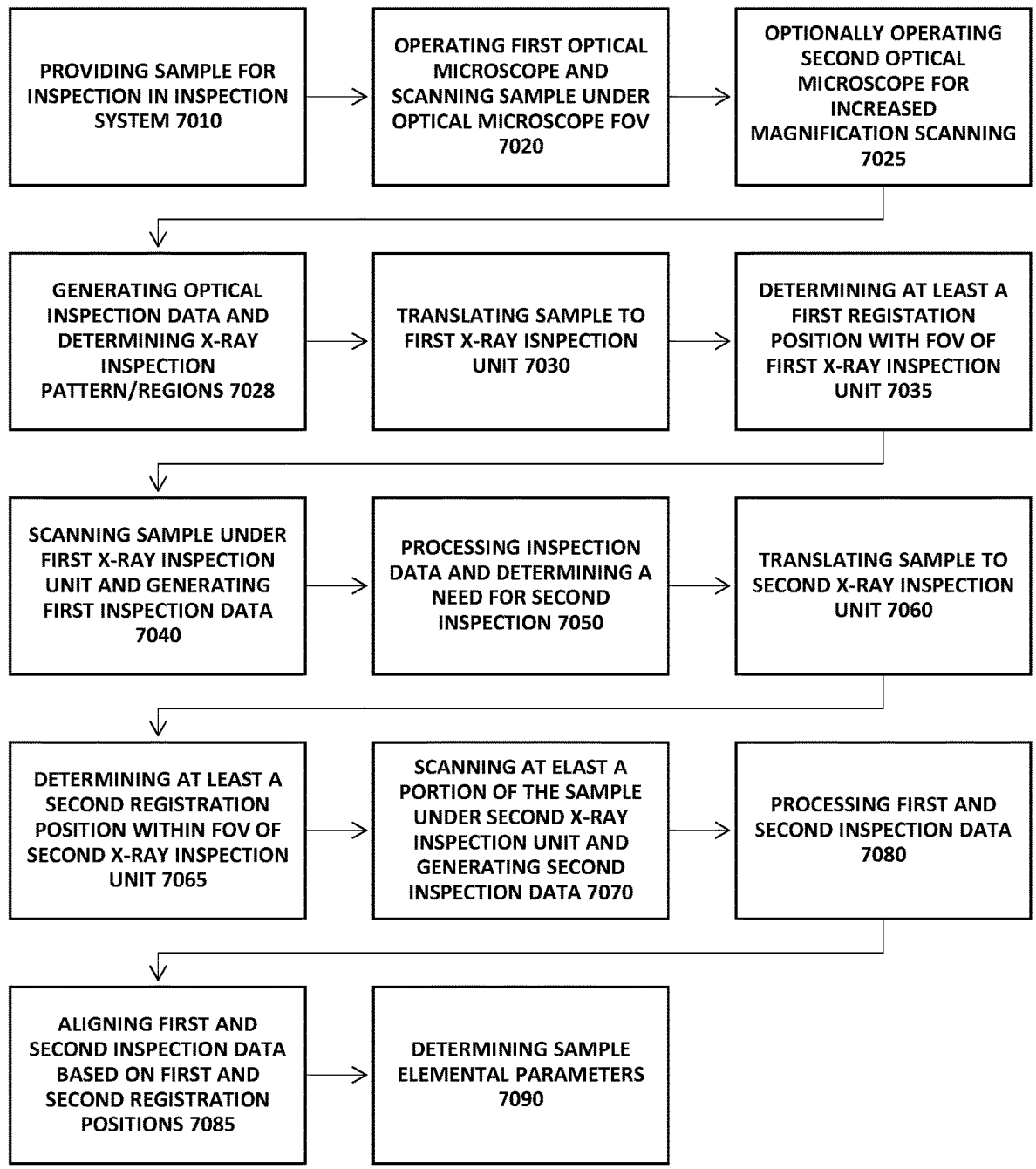
FIG. 7 illustrates a block diagram exemplifying inspection of a sample using the inspection system according to some embodiments of the present disclosure.

For examples, FIG. 7 illustrates a flow of inspection of a sample using the inspection system according to some embodiments of the present disclosure. To initiate inspection, a sample is provided into the inspection system 7010 and placing the sample on the moveable stage. As indicated above, the inspection system of the present disclosure simplifies inspection using two or more different inspection parameters as the sample may be maintained within the system between inspection sessions. In some embodiments, the sample may be first inspected optically using an optical microscope 7020. The optical inspection generally includes scanning and imaging of the sample using a first optical microscope and may optically include the use of a second optical microscope 7025, e.g., providing increased magnification to focus on one or more selected regions of the sample. The optical inspection data provides a magnified image of the sample. This image data may be used 7028 to determine inspection pattern for x-ray inspection including one or more regions of the sample to be inspected with the first and/or second inspection units.

For inspection using the X-ray inspection units, the moveable stage is typically operable for translating the sample to a selected location associated with field of view (FOV) of the first x-ray inspection unit 7030. Generally, the first x-ray inspection unit here may utilize a polychromatic inspection or provide inspection with relatively larger field of view. To initiate inspection, at least a first registration position may be determined 7035, this is to allow comparison between the optical inception and the one or more x-ray inspection data. To properly inspect the sample, the first x-ray inspection unit is operated, and its operation may be combined with scanning the sample under the first x-ray inspection unit to inspect one or more selected regions of the sample 7040. The first x-ray inspection unit thus generate a first output inspection data indicative of x-ray fluorescence mapping of the inspected region. Typically, in some embodiments, the output inspection data may be transmitted to a computer system including one or more processors for processing. The processing may include comparison of the inspection data to selected reference data, and may include determining a need for second inspection, using a second x-ray inspection unit having selected different parameters, in one or more regions of the sample 7050.

A decision on need for second inspection, and selection of one or more regions to be inspected may be determined based on required inspection resolution, detection of one or more elements that are present in low concentrations/amounts in one or more regions (e.g., bumps) of the sample. The decision may also relate to the types and inspection characteristics of the first and second x-ray inspection units. For example, when utilizing a first polychromatic inspection unit and a second monochromatic inspection unit, the need for additional inspection may relate to regions of the sample including low-concentration elements that need to be inspected with enhanced detection.

To initiate second x-ray inspection, the stage is operated for translating the sample to the second x-ray inspection unit 7060, and at least a second registration position may be determined 7065. The second x-ray inspection unit is operated, and the stage is shifted for scanning the sample 7070, or at least one or more selected regions of the sample. The second x-ray inspection unit generated a second output inspection data and the first and second output inspection data may be processed 7080 for determining data on the sample. To simplify processing, the first and second output inspection data may be aligned in accordance with first and second registration positions 7085. When utilizes x-ray fluorescence inspection, the aligned first and second output inspection data provides data on elemental components of selected regions in the sample 7090. This output data may provide data on elements existing in high concentrations as well as elements existing in low concentrations, which are detectable using monochromatic x-ray inspection as described above.

It should be noted that the terms first and second are used with reference to FIG. 7 to relate to order of inspection. Generally, the first inspection may be performed by the second polychromatic x-ray inspection unit and the second inspection may be performed using the first monochromatic x-ray inspection unit.

It is to be noted that the various features described in the various embodiments can be combined according to all possible technical combinations.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and systems for carrying out the several purposes of the presently disclosed subject matter.

Those skilled in the art will readily appreciate that various modifications and changes can be applied to the embodiments of the invention as hereinbefore described without departing from its scope, defined in and by the appended claims.

The invention claimed is:

1. A sample inspection system, comprising:
at least first and second inspection units positioned above a sample region, each of said at least first and second inspection units comprises at least one X-ray radiation source and respective detector arrangement and configured for X-ray fluorescent inspection of a sample; wherein said at least first and second x-ray inspection units provide first and second inspection properties different in at least one of: bandwidth of emitted X-ray energies, energy of emitted X-rays, spot size of X-ray beam generated on a sample.

2. The sample inspection system of claim 1, wherein at least one of said first or second X-ray inspection units comprise at least one monochromatic X-ray radiation source.

3. The sample inspection system of claim 1, wherein said first and second X-ray inspection units are configured to provide monochromatic X-ray illumination having one or more central illumination energies with bandwidth of up to 2 KeV around said one or more central illumination energies, and wherein said first and second inspection units provide first and second inspection properties different in at least one of: said one or more central illumination energies of emitted X-rays and spot size of X-ray beam generated on a sample.

4. The sample inspection system of claim 1, wherein said first inspection unit is configured to emit X-ray radiation formed of one or more discrete energy bands, and said second inspection unit is configured to emit continuous spectrum of polychromatic X-ray radiation.

5. The sample inspection system of claim 4, wherein said first inspection unit comprises an optical arrangement comprising one or more multilayer optical elements configured to provide band-pass filtering to X-ray radiation directed thereon, thereby providing illumination pattern having one or more discrete energy bands.

6. The sample inspection system of claim 1, wherein said at least first and second inspection units are mounted on a common mounting arrangement, said common mounting arrangement comprises a horizontal beam positioned above said sample region, said horizontal beam is supported by at least two support beams located at different sides of said dedicated sample region.

7. The sample inspection system of claim 6, wherein said horizontal beam is supported by the at least two support beams, each of said support beams are formed having a first, generally vertical, portion extending upward from a bottom frame of said system and a second, generally horizontal, portion extending horizontally from said first portion and connected to said horizontal beam.

8. The sample inspection system of claim 6, wherein said at least two support beams are formed as an inverted "L" shape, having generally horizontal portion extending above said dedicated sample region and placing said horizontal beam above said dedicated sample region.

9. The sample inspection system of claim 6, further comprising at least first and second optical microscope units having respectively first and second different focal lengths, thereby enabling adjustment of field of view for optical microscopy while obviating the need for moving optical elements during sample inspection.

10. The sample inspection system of claim 6, wherein said at least first and second inspection units are mounted on said horizontal beam via respective first and second dedicated connectors, said first and second dedicated connectors comprise a horizontal portion configured to mount said connector on a top surface of said horizontal beam and a vertical portion extending along a vertical wall of said horizontal beam, and wherein said vertical portion is connectable to the respective one of said at least first and second inspection units.

11. The sample inspection system of claim 10, wherein at least one of said first or second connectors further comprises a lower edge positioned to lock onto a bottom part of said horizontal beam.

12. The sample inspection system of claim 1, further comprising a moveable sample platform positioned in said sample inspection region and adapted for placing a sample for inspection, said moveable sample mount has planar moving range enabling inspection by each one of said at least first and second inspection units.

13. The sample inspection system of claim 1, wherein elements of said at least first and second inspection units are stationary during sample inspection, thereby eliminating sample contamination associated with moving elements above the sample.

14. A system, comprising:
a chassis structure;
a sample mount configured for holding one or more samples and enabling translation of said one or more samples within a sample region;
an inspection system mounting arrangement comprising at least first and second support beams attached to said chassis, said at least first and second support beams comprise at least horizontal portion stretching above said sample region; and
a horizontal beam mounted on said at least first and second support beams and positioned above said sample region, said horizontal beam comprises mounting arrangement for mounting at least first and second X-ray fluorescence inspection units simultaneously, to enable operation of said at least first and second X-ray fluorescence inspection units by translation shifts of a sample within said sample region.

15. The system of claim 14, wherein said at least first and second support beams comprise a vertical portion attached to said chassis laterally to said sample region, and wherein said at least horizontal portion extends from a top part of said vertical portion above said sample region, and wherein mounting arrangement of said horizontal beam are placed above said sample region.

16. The system of claim 14, wherein said mounting arrangement for mounting at least first and second X-ray fluorescence inspection units comprise attachment points on at least two of top, side, and bottom surfaces of said horizontal beam.

17. The system of claim 14, further comprising at least first and second X-ray fluorescence inspection units mounted on the respective mounting arrangement, each of said at least first and second X-ray fluorescence inspection unit comprises at least one X-ray radiation source and respective detector arrangement; wherein said first inspection unit comprises one or more multilayer radiation filters configured to filter X-ray radiation to provide inspection using one or more discrete energy bands, and said second inspection unit is configured to emit continuous polychromatic X-ray radiation.

18. The system of claim 14, wherein said sample mount comprises translation arrangement enabling selective translation of a sample within said sample region allowing selective positioning of said sample below each one of mounting arrangement positions.

19. A method for X-ray fluorescence (XRF) inspection of a sample, the method comprising:
providing said sample to an inspection system;
inspecting said sample using a first x-ray inspection unit having first set of inspection properties and generating first output inspection data;
processing said first output inspection data and determining one or more regions of said sample to be inspected by a second x-ray inspection unit;
translating said sample within said inspection system to location of a second x-ray inspection unit;
inspecting said sample using a second x-ray inspection unit having second set of inspection properties and generating second output inspection data;
aligning said first and second output inspection data and processing said first and second output inspection to determine sample properties.

20. The method of claim 19, further comprising:
determining a first registration position associated with inspection using said first x-ray inspection unit;
determining a second registration position associated with inspection using said second x-ray inspection unit;
using said first and second registration positions for aligning said first and second output inspection data.

* * * * *